«12» United States Patent
Lattmann et al.

(10) Patent No.: US 7,074,815 B2
(45) Date of Patent: *Jul. 11, 2006

(54) 4-[3,5-BIS-(2-HYDROXY-PHENYL)-[1,2,4] TRIAZOL-1-YL]-BENZOIC ACID DERIVATIVES FOR TREATING AN EXCESS OF METAL IN THE BODY

(75) Inventors: Rene Lattmann, Oberwil (CH); Felix Waldmeier, Oberwil (CH)

(73) Assignee: Novartis AG, Basel (CH)

( * ) Notice: Subject to any disclaimer, the term of this patent is extended or adjusted under 35 U.S.C. 154(b) by 68 days.

This patent is subject to a terminal disclaimer.

(21) Appl. No.: 10/491,310

(22) PCT Filed: Nov. 5, 2002

(86) PCT No.: PCT/EP02/12342

§ 371 (c)(1),
(2), (4) Date: Mar. 29, 2004

(87) PCT Pub. No.: WO03/039341

PCT Pub. Date: May 15, 2003

(65) Prior Publication Data

US 2005/0080120 A1   Apr. 14, 2005

(30) Foreign Application Priority Data

Nov. 6, 2001   (GB) ................... 0126618.8

(51) Int. Cl.
C07D 249/08 (2006.01)
A61K 31/42 (2006.01)

(52) U.S. Cl. .................... 514/383; 548/269.4
(58) Field of Classification Search ................ 514/383; 548/269.4
See application file for complete search history.

(56) References Cited

U.S. PATENT DOCUMENTS 6,465,504 B1 * 10/2002 Lattmann et al. .......... 514/383
6,596,750 B1 *  7/2003 Lattmann et al. .......... 514/383
6,723,742 B1 *  4/2004 Lattmann et al. .......... 514/383

FOREIGN PATENT DOCUMENTS

WO    WO 97/49395    12/1997

OTHER PUBLICATIONS

Heinz, et al. 4-[3,5-Bis(2-hydroxyphenyl)-1,2,4-triazol-1-yl]-benzoic acid: A Novel Efficient and Selective Iron (III) Complexing Agent. Angew. Chemie Int. Ed., vol. 38, No. 17, pp. 2568-2570 (1999).*

Heinz, U. et al., "4-[3,5-Bis(2-hydroxyphenyl)-1,2,4-triazol-1-yl]-benzoic Acid: A Novel Efficient and Selective Iron(III) Complexing Agent," Angew. Chemie Int. Ed., vol. 38, No. 17, pp. 2568-2570 (1999).

Rouan M.C., "Determination of a new oral iron chelator, ICL670, and its iron complex in plasma by high-performance liquid chromatography and ultraviolet detection," Journal of Chromatography B, vol. 755, pp. 203-213 (2001).

* cited by examiner

*Primary Examiner*—Kamal A. Saeed
*Assistant Examiner*—Susannah L. Chung
(74) *Attorney, Agent, or Firm*—Oona A. Jackson

(57) ABSTRACT

The present invention provides new 4-[3,5-bis-(2-hydroxyphenyl)-[1,2,4]triazol-1-yl]-benzoic acid derivatives which can be used in the treatment of diseases which cause an excess of metal in the human or animal body or are caused by it.

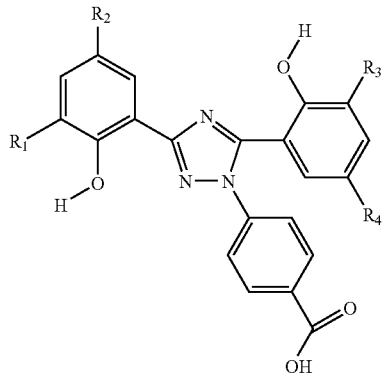

6 Claims, No Drawings

4-[3,5-BIS-(2-HYDROXY-PHENYL)-[1,2,4] TRIAZOL-1-YL]-BENZOIC ACID DERIVATIVES FOR TREATING AN EXCESS OF METAL IN THE BODY

Various disorders of warm-blooded animals are linked with an excess of metals, in particular trivalent metals, in the body tissues. For example aluminium in dialysis encephalopathy and osteomalacia, as well as in Alzheimer's disease. In other illnesses, in particular of man, an excess of iron occurs in the various tissues. This is designated as iron overload (formerly haemosiderosis). It occurs, for example, after parenteral administration of iron (especially repeated blood transfusions) or after increased uptake of iron from the gastrointestinal tract. Repeated transfusions are necessary in serious anaemias, especially in thalassaemia major, the severe form of β-thalassaemia, but also in other anaemias. Increased iron absorption from the gastrointestinal tract either takes place primarily, e.g. on account of a genetic defect (so-called haemochromatosis), or secondarily, such as after anaemias in which blood transfusions are not necessary, for example thalassaemia intermedia, a milder form of β-thalassaemia.

Untreated iron overload can cause severe organ damage, in particular of the liver, the heart and the endocrine organs, and can lead to death. Iron chelators are able to mobilize and excrete the iron deposited in the organs and thus lower the iron-related morbidity and mortality.

A reduction in the iron(III) concentration is also of interest for the treatment of disorders due to iron(III)-dependent microorganisms and parasites, which is of key importance not only in human medicine, such as in particular in malaria, but also in veterinary medicine. Complexing of other metals, in partcular trivalent metals, can also be used for excretion thereof from the organism. A number of further applications are also described in the literature, e.g. by G. Kontoghiorghes, *Toxicology Lett.* 80, 1–18 (1995).

Desferrioxamine B has already been known for a long time and used therapeutically for these purposes (H. Bickel, H. Keberle and E. Vischer, *Helv. Chim. Acta* 46, 1385–9 [1963]). A disadvantage of this preparation, however, turns out to be the fact that desferrioxamine and its salts only have a low, inadequate activity on oral administration and require a parenteral administration form in all of the abovementioned application possibilities. It is thus recommended, for example, as a particularly effective method to administer the active substance by means of a slow (8- to 12-hour) subcutaneous infusion, which, however, demands the use of a portable mechanical device, such as an infusion syringe actuated by an electrical drive. Apart from their awkwardness, such solutions are affected by a high treatment cost, which severely restricts their use; in particular a comprehensive treatment of the thalassaemias in the countries of the Mediterranean region, of the Middle East, India and South-East Asia, of malaria worldwide and of sickle-cell anaemia in African countries is made impossible. These widespread diseases are furthermore a serious problem for the health service in these countries and make the search for a simpler and more inexpensive therapy, preferably by means of an orally active preparation, the urgent object in this area.

The present invention provides new 4-[3,5-bis-(2-hydroxy-phenyl)-[1,2,4]triazol-1-yl]-benzoic acid derivatives which can be used in the treatment of diseases which cause an excess of metal in the human or animal body or are caused by it.

The present invention relates to compounds of the formula I

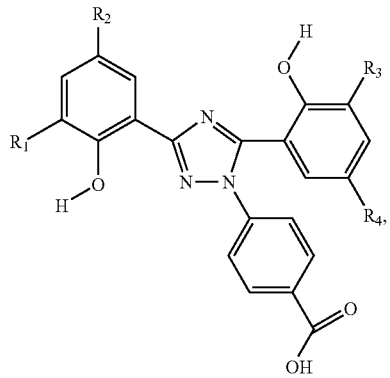

wherein one of the radicals $R_1$, $R_2$, $R_3$ and $R_4$ is hydroxy and the remaining radicals are each independently of the others hydrogen or hydroxy;

and salts thereof.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts.

In the presence of negatively charged radicals, such as carboxy or sulfo, salts may also be formed with bases, e.g. metal or ammonium salts, such as alkali metal or alkaline earth metal salts, or ammonium salts with ammonia or suitable organic amines, such as tertiary monoamines.

In the presence of a basic group and an acid group in the same molecule, a compound of formula I may also form internal salts.

For isolation or purification purposes it is also possible to use pharmaceutically unacceptable salts, for example picrates or perchlorates. Only the pharmaceutically acceptable salts or free compounds (if the occasion arises, in the form of pharmaceutical compositions) attain therapeutic use, and these are therefore preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

The compounds of formula I have valuable pharmacological properties when used in the treatment of disorders which cause an excess of metal in the human or animal body or are caused by it, primarily a marked binding of trivalent metal ions, in particular those of iron (A. E. Martell and R. J. Motekaitis, "Determination and Use of Stability Constants", VCH Publishers, New York 1992). They are able, for example in an animal model using the non-iron overloaded cholodocostomized rat (R. J. Bergeron et al., *J. Med. Chem.* 34, 2072–2078 (1991)) or the iron-overloaded monkey (R. J. Bergeron et al., *Blood* 81, 2166–2173 (1993)) in doses from approximately 5 μmol/kg, inter alia, to prevent the deposition of iron-containing pigments and in the case of existing iron deposits in the body cause excretion of the iron.

Very special preference is given to a compound of the formula I which is selected from the group consisting of 4-[3-(2,3-dihydroxy-phenyl)-5-(2-hydroxy-phenyl)-[1,2,4]triazol-1-yl]-benzoic acid, [3-(2,5-dihydroxy-phenyl)-5-(2-hydroxy-phenyl)-[1,2,4]triazol-1-yl]-benzoic acid, 4-[5-(2,5-dihydroxy-phenyl)-3-(2-hydroxy-phenyl)-[1,2,4]triazol-1-yl]-benzoic acid, and salts thereof.

A compound of the invention may be prepared by processes known per se for other compounds. In particular, they can be prepared by the processes described in e.g. WO 97/49395.

In the preferred embodiment, a compound of the formula I is prepared according to the processes and process steps defined in the Examples below.

Pharmaceutical Compositions, Methods, and Uses

In particular, the invention relates to the use of a compound of formula I for the treatment of diseases which cause an excess of iron in the human or animal body or are caused by it, preferably in the form of pharmaceutically acceptable preparations, in particular in a method for the therapeutic treatment of the human body, and to a treatment method of this type.

In addition, the invention relates to novel preparations, comprising at least one compound of the formula I and salts thereof; and at least one pharmaceutically acceptable carrier; and to methods for their preparation. These pharmaceutical preparations are those for enteral, in particular oral, and furthermore rectal, administration and those for parenteral administration to warm-blooded animals, especially to man, the pharmacological active ingredient being contained on its own or together with customary pharmaceutical adjuncts. The pharmaceutical preparations contain (in percentages by weight), for example, from approximately 0.001% to 100%, preferably from approximately 0.1% to approximately 100%, of the active ingredient.

Pharmaceutical preparations for enteral or parenteral administration are, for example, those in unit dose forms, such as sugar-coated tablets, tablets, dispersible tablets, effervescent tablets, capsules, suspendable powders, suspensions or suppositories, or ampoules. These are prepared in a manner known per se, e.g. by means of conventional pan-coating, mixing, granulation or lyophilization processes. Pharmaceutical preparations for oral administration can thus be obtained by combining the active ingredient with solid carriers, if desired granulating a mixture obtained and processing the mixture or granules, if desired or necessary, after addition of suitable adjuncts to give tablets or sugar-coated tablet cores.

Suitable carriers are, in particular, fillers such as sugars, e.g. lactose, sucrose, mannitol or sorbitol, cellulose preparations and/or calcium phosphates, e.g. tricalcium phosphate or calcium hydrogen phosphate, furthermore binders, such as starch pastes, using, for example, maize, wheat, rice or potato starch, gelatin, tragacanth, methylcellulose and/or polyvinylpyrrolidone, and, if desired, disintegrants, such as the abovementioned starches, furthermore carboxymethyl starch, crosslinked polyvinylpyrrolidone, agar or alginic acid or a salt thereof, such as sodium alginate. Adjuncts are primarily flow-regulating and lubricating agents, e.g. salicylic acid, talc, stearic acid or salts thereof, such as magnesium or calcium stearate, and/or polyethylene glycol. Sugar-coated tablet cores are provided with suitable, if desired enteric, coatings, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of enteric coatings, solutions of suitable cellulose preparations, such as acetylcellulose phthalate or hydroxypropylmethylcellulose phthalate. Colorants or pigments, e.g. for the identification or the marking of various doses of active ingredient, can be added to the tablets or sugar-coated tablet coatings.

Dispersible tablets are tablets which rapidly disintegrate in a comparatively small amount of liquid, e.g. water, and which, if desired, contain flavourings or substances for masking the taste of the active ingredient. They can advantageously be employed for the oral administration of large individual doses, in which the amount of active ingredient to be administered is so large that on administration as a tablet which is to be swallowed in undivided form or without chewing that it can no longer be conveniently ingested, in particular by children. Further orally administrable pharmaceutical preparations are hard gelatin capsules and also soft, closed capsules of gelatin and a plasticizer, such as glycerol or sorbitol. The hard gelatin capsules can contain the active ingredient in the form of granules, e.g. as a mixture with fillers, such as lactose, binders, such as starches, and/or glidants, such as talc or magnesium stearate, and, if desired, stabilizers. In soft capsules, the active ingredient is preferably dissolved or suspended in suitable liquids, such as fatty oils, liquid paraffin or liquid polyethylene glycols, it also being possible to add stabilizers.

Moreover, suspendable powders, e.g. those which are described as "powder in bottle", abbreviated "PIB", or ready-to-drink suspensions, are suitable for an oral administration form. For this form, the active ingredient is mixed, for example, with pharmaceutically acceptable surface-active substances, for example, sodium lauryl sulfate or polysorbate, suspending auxiliaries, e.g. hydroxypropylcellulose, hydroxypropylmethylcellulose or another known from the prior art and previously described, for example, in "Handbook of Pharmaceutical Ecipients", pH regulators, such as citric or tartaric acid and their salts or a USP buffer and, if desired, fillers, e.g. lactose, and further auxiliaries, and dispensed into suitable vessels, advantageously single-dose bottles or ampoules. Immediately before use, a specific amount of water is added and the suspension is prepared by shaking. Alternatively, the water can also be added even before dispensing.

Rectally administrable pharmaceutical preparations are, for example, suppositories which consist of a combination of the active ingredient with a suppository base. A suitable suppository base is, for example, natural or synthetic triglycerides, paraffin hydrocarbons, polyethylene glycols or higher alkanols. Gelatin rectal capsules can also be used which contain a combination of the active ingredient with a base substance. Possible base substances are, for example, liquid triglycerides, polyethylene glycols or paraffin hydrocarbons.

For parenteral administration, aqueous solutions of an active ingredient in water-soluble form, e.g. of a water-soluble salt, are primarily suitable; furthermore suspensions of the active ingredient, such as appropriate oily injection suspensions, suitable lipophilic solvents or vehicles, such as fatty oils, e.g. sesame oil, or synthetic fatty acid esters, e.g. ethyl oleate or triglycerides, being used, or aqueous injection suspensions which contain viscosity-increasing substances, e.g. sodium carboxymethylcellulose, sorbitol and/or dextran, and, if desired, also stabilizers.

The dosage of the active ingredient can depend on various factors, such as activity and duration of action of the active ingredient, severity of the illness to be treated or its symptoms, manner of administration, warm-blooded animal species, sex, age, weight and/or individual condition of the warm-blooded animal. The doses to be administered daily in the case of oral administration are between 10 and approximately 120 mg/kg, in particular 20 and approximately 80 mg/kg, and for a warm-blooded animal having a body weight of approximately 40 kg, preferably between approximately 400 mg and approximately 4,800 mg, in particular approximately 800 mg to 3,200 mg, which is expediently divided into 2 to 12 individual doses.

Preferably, the invention relates to novel preparations comprising at least one compound of the formula I and salts thereof; and at least one pharmaceutically acceptable carrier, and to methods for their preparation. These pharmaceutical preparations are those for enteral, in particular oral, and furthermore rectal, administration, and those for parenteral administration to warm-blooded animals, especially to man, the pharmacological active ingredient being present on its own or together with customary pharmaceutical adjuncts. The pharmaceutical preparations contain (in percentages by weight), for example, from approximately 0.001% to 100%, preferably from approximately 0.1% to approximately 50%, of the active ingredient.

EXAMPLES

The following Examples serve to illustrate the invention without limiting its scope.

Temperatures are measured in degrees Celsius. Unless otherwise indicated, the reactions take place at room temperature.

The $R_f$ values which indicate the ratio of the distance moved by each substance to the distance moved by the eluent front are determined on silica gel thin-layer plates (Merck, Darmstadt, Germany) by thin-layer chromatography using the respective named solvent systems.

The analytical HPLC conditions are as follows:

| | |
|---|---|
| Instrument: | HP-1100 System with G1311A quaternery pump (0.8 ml dead volume), G1313A autosampler, G1316A column compartment (35° C.), G1315A diode array detector and G1946A mass spectrometer. |
| Column: | Waters Symmetry C8, 50 × 2.1 mm 3.5 μm mean particle size. Detection by UV absorption at 210–250 nm. The retention times ($t_R$) are given in minutes. Flow rate: 0.5 ml/min. |
| Gradient: | 5% → 95% b) in a) within 6.5 min. a): water + 5% acetonitrite + 0.1% TFA b): Acetonitrile + 0.1% TFA. |

The short forms and abbreviations used have the following definitions:
h hour(s)
MS-ES mass spectroscopy (electron spray)
min minute(s)
m.p. melting point
MS-APCI⁺ mass spectroscopy (atomic pressure chemical ionisation)
$t_R$ retention times.

Example 1

4-[3-(2,3-Dihydroxy-phenyl)-5-(2-hydroxy-phenyl)-[1,2,4]triazol-1-yl]benzoic acid (M2)

A mixture of 5.5 g of 2-(2,3-dihydroxy-phenyl)benzo[e][1,3]oxazin-4-one with 8-hydroxy-2-(2-hydroxy-phenyl)-benzo[e][1,3]oxazin-4-one and 3.3 g 4-hydrazino-benzoic acid in 50 ml of ethanol is heated to reflux for 2. The mixture is evaporated to dryness and the product is isolated by preparative HPLC; HPLC $t_R$=5.15 min, MS-APCI⁺: (M+H)⁺=390, m.p.: 223–226° C.

Step 1.1: Mixture of 2-(2,3-Dihydroxy-phenyl)-benzo[e][1,3]oxazin-4-one with 8-Hydroxy-2-(2-hydroxy-phenyl)-benzo[e][1,3]oxazin-4-one A mixture of 10 g 2,3-dihydroxy-benzoic acid, 7.5 g 2-hydroxy-benzamide and 0.5 ml pyridine in 50 ml toluene is heated under reflux. 8.8 ml of thionylchloride is added over a period of 1 h. The mixture is kept under reflux for another hour, cooled to 40° C. and 100 ml ethanol are added. After cooling to 5° C. the precipitated product is filtered off and washed with cold ethanol; HPLC $t_R$=4.63 min, MS-APCI⁺: (M+H)⁺=256.

Example 2

4-[3-(2,5-Dihydroxy-phenyl)-5-(2-hydroxy-phenyl)-[1,2,4]triazol-1-yl]-benzoic acid (M1) and 4-[5-(2,5-Dihydroxy-phenyl)-3-(2-hydroxy-phenyl)-[1,2,4]triazol-1-yl]-benzoic acid (M4)

A mixture of 5 g of 4-[3-(2-hydroxy-5-methoxy-phenyl)-5-(2-hydroxy-phenyl)-[1,2,4]triazol-1-yl]-benzoic acid with 4-[5-(2-hydroxy-5-methoxy-phenyl)-3-(2-hydroxy-phenyl)-[1,2,4]triazol-1-yl]-benzoic acid is dissolved in 40 ml acetic acid and 40 ml aqueous hydrogen bromide (45%) and heated under reflux for 3 h. The solvents are evaporated and the residue is suspended in hot water and filtered. The two isomeric products are separated by preparative HPLC:

M1: HPLC $t_R$=4.95 min, MS-APCI⁺: (M+H)⁺=390, m.p.: 297–299° C.;
M4: HPLC $t_R$=5.25 min, MS-APCI⁺: (M+H)⁺=390, m.p.: 312–315° C.

Step 2.1: Mixture of 2-(2-Hydroxy-phenyl)-6-methoxy-benzo[e][1,3]oxazin-4-one with 2-(2-hydroxy-5-methoxy-phenyl)benzo[e][1,3]oxazin-4-one A mixture of 11 g 2-hydroxy-5-methoxy-benzoic acid, 7.5 g 2-hydroxy-benzamide and 0.5 ml pyridine in 50 ml xylene is heated under reflux. 8.8 ml of thionylchloride is added over a period of 1 h. The mixture is kept under reflux for another hour, cooled to 40° C. and 100 ml ethanol are added. After cooling to 5° C. the precipitated product is filtered off and washed with cold ethanol; HPLC $t_R$=5.23 & 5.41 min, MS-APCI⁺: (M+H)⁺=270.

Step 2.2: Mixture of 4-[3-(2-Hydroxy-5-methoxy-phenyl)-5-(2-hydroxy-phenyl)-[1,2,4]triazol-1-yl]-benzoic acid with 4-[5-(2-Hydroxy-5-methoxy-phenyl)-3-(2-hydroxy-phenyl)-[1,2,4]triazol-1-yl]-benzoic acid A mixture of 7 g of 2-(2-hydroxy-phenyl)₆-methoxy-benzo[e][1,3]oxazin-4-one with 2-(2-hydroxy-5-methoxy-phenyl)-benzo[e][1,3]oxazin-4-one and 4 g 4-hydrazino-benzoic acid in 70 ml of ethanol are heated to reflux for 1 h. The mixture is evaporated to dryness; HPLC $t_R$=5.56 & 5.67 min, MS-APCI⁺: (M+H)⁺=404.

The invention claimed is:

1. A compound of the formula I

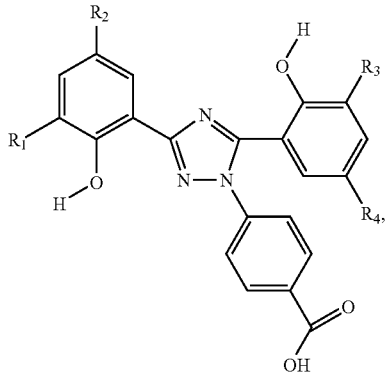

wherein one of the radicals $R_1$, $R_2$, $R_3$ and $R_4$ is hydroxy and the remaining radicals are each independently of the others hydrogen or hydroxy;

or a salt thereof.

2. A compound of the formula I according to claim 1, which is 4-[3-(2,3-dihydroxy-phenyl)-5-(2-hydroxy-phenyl)-[1,2,4]triazol-1-yl]-benzoic acid, or a salt thereof.

3. A compound of the formula I according to claim 1, which is 4-[3-(2,5-dihydroxy-phenyl)-5-(2-hydroxy-phenyl)-[1,2,4]triazol-1-yl]-benzoic acid, or a salt thereof.

4. A compound of the formula I according to claim 1, which is 4-[5-(2,5-dihydroxy-phenyl)-3-(2-hydroxy-phenyl)-[1,2,4]triazol-1-yl]-benzoic acid, or a salt thereof.

5. A pharmaceutical preparation comprising the compound of claim 1 together with at least one pharmaceutically acceptable carrier.

6. A method of treating excess iron in a human or animal body comprising the compound of claim 1.

* * * * *